United States Patent
Debevec et al.

(10) Patent No.: US 6,919,962 B2
(45) Date of Patent: Jul. 19, 2005

(54) REFLECTOMETRY APPARATUS AND METHOD

(75) Inventors: Paul E. Debevec, Marina del Rey, CA (US); Andrew J. Gardner, Marina del Rey, CA (US); Timothy S. Hawkins, Marina del Rey, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/774,173

(22) Filed: Feb. 7, 2004

(65) Prior Publication Data

US 2004/0227948 A1 Nov. 18, 2004

Related U.S. Application Data

(60) Provisional application No. 60/446,003, filed on Feb. 7, 2003.

(51) Int. Cl.$^7$ ................................................ G01N 21/55
(52) U.S. Cl. .................................................... 356/445
(58) Field of Search .......................... 356/445; 382/141

(56) References Cited

U.S. PATENT DOCUMENTS

| | | | | |
|---|---|---|---|---|
| 4,908,717 A | * | 3/1990 | Natori | 358/474 |
| 5,644,392 A | * | 7/1997 | Soest et al. | 356/237.1 |
| 6,450,664 B1 | * | 9/2002 | Kelly | 362/249 |
| 6,462,813 B1 | * | 10/2002 | Haven et al. | 356/237.2 |
| 2002/0075531 A1 | * | 6/2002 | Rhoads | 358/533 |
| 2003/0128362 A1 | * | 7/2003 | Gudaitis et al. | 356/405 |

* cited by examiner

*Primary Examiner*—Zandra V. Smith
(74) *Attorney, Agent, or Firm*—McDermott Will & Emery LLP

(57) ABSTRACT

A reflectometry apparatus and method is presented that allow the diffuse and specular reflectance parameters of an object to be independently and reliably measured, and that allow the variations in surface normal and surface height to be estimated. An extended light source having an elongated configuration, for example a linear cylindrical light source such as a neon tube, is moved across the surface of an object while a digital camera detects the reflected light to acquire a series of images of the object surface. A reflectance trace table is synthesized for a range of model parameters using a virtualized rendition of the linear light source. For each pixel, the observed reflectances are compared to the synthesized reflectance trace table, to determine the reflectance parameters that most closely match the observed data.

33 Claims, 5 Drawing Sheets

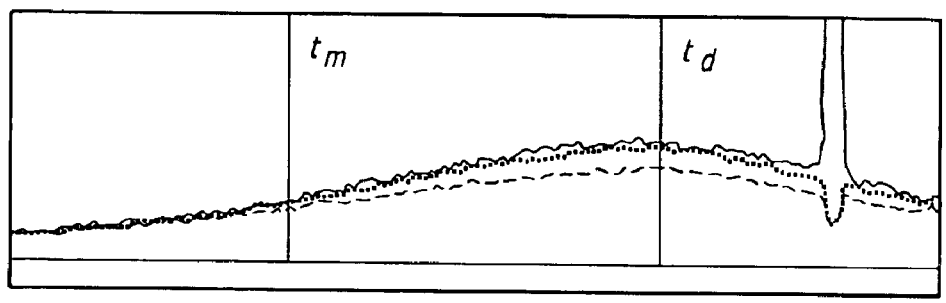
FIG. 2A  Diffuse Vellum
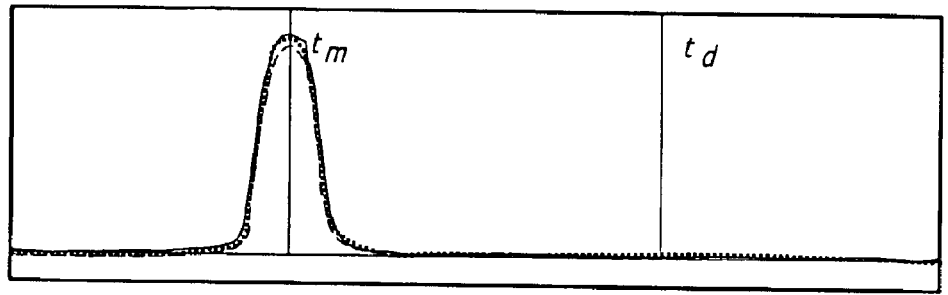
FIG. 2B  Shiny Black Paper
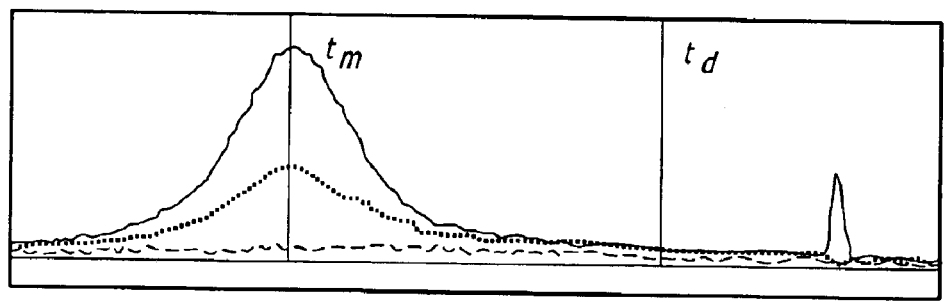
FIG. 2C  Gold
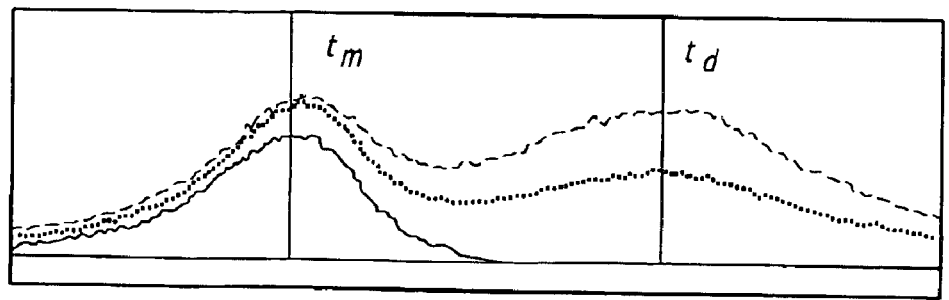
FIG. 2D  Blue Decal

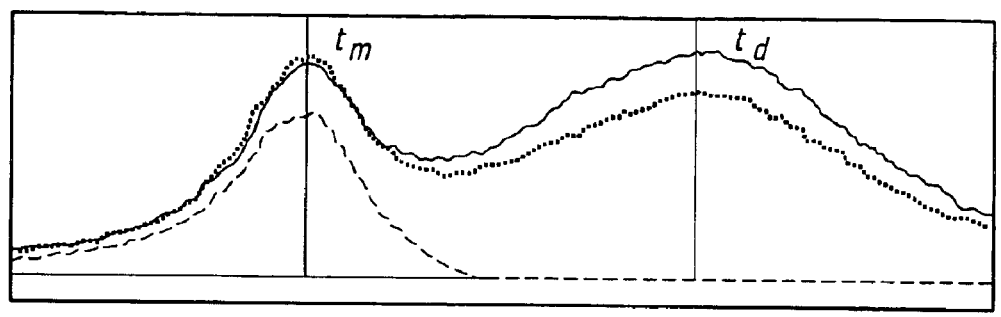
FIG. 4A — Original Reflectance Trace
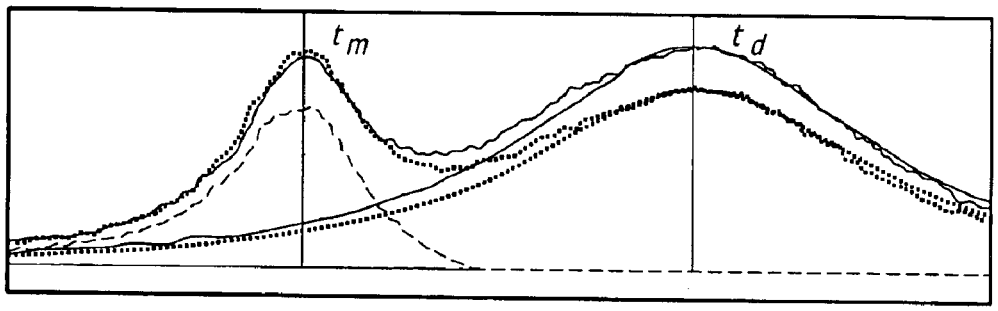
FIG. 4B — Fitted Diffuse Lobe
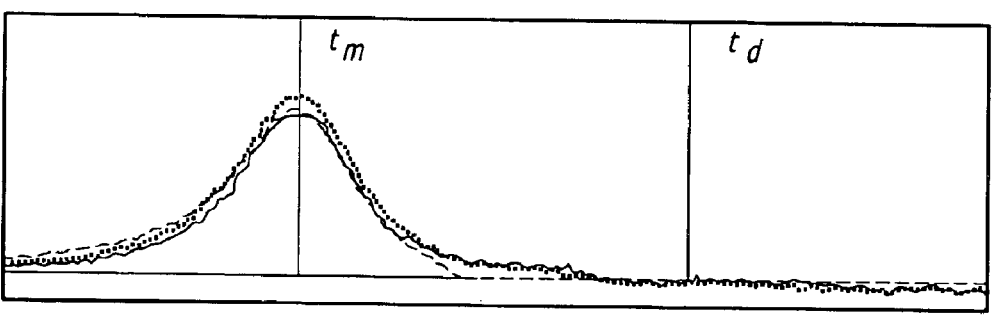
FIG. 4C — After Subtracting Diffuse Lobe
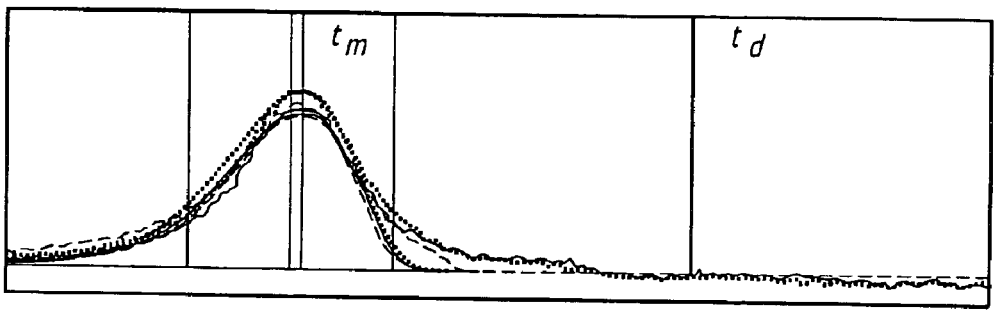
FIG. 4D — Fitted Specular Lobe

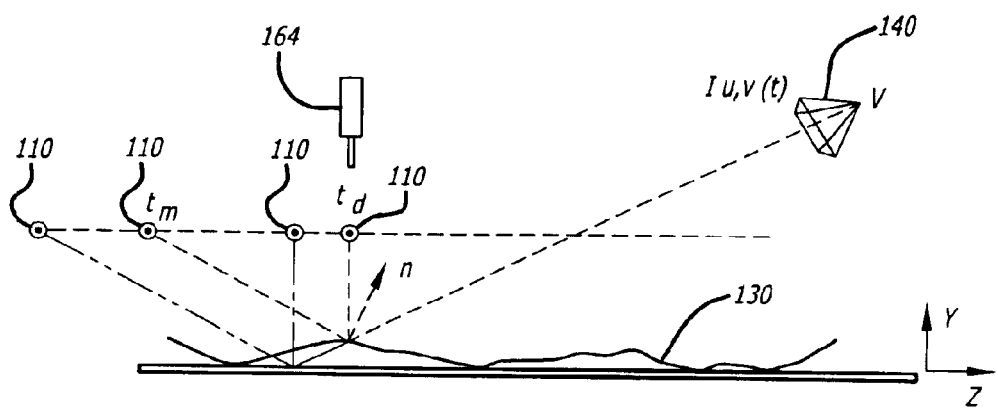
FIG. 5
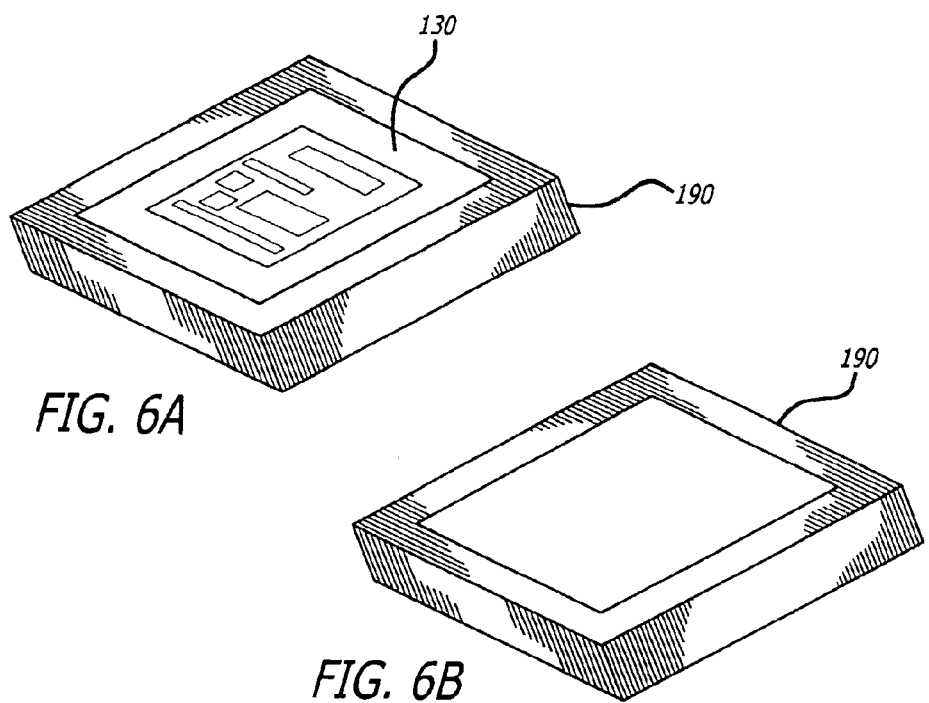
FIG. 6A
FIG. 6B

REFLECTOMETRY APPARATUS AND METHOD

CROSS REFERENCE TO RELATED APPLICATIONS

This application claims the benefit of priority under 35 U.S.C. §119(e) from co-pending, commonly owned U.S. provisional patent application, Ser. No. 60/446,003, filed on Feb. 7, 2003, entitled "Linear Light Source Reflectometry Software." The entire content of this provisional application is incorporated herein by reference.

BACKGROUND

The wide range of optical properties that are exhibited by materials provides a useful source of information about the identity of the materials. Different materials reflect, scatter, absorb, and transmit light in different ways, allowing the materials to be distinguished by measuring these optical properties. In particular, a lot of materials tend to reflect most of the light that is incident on their surfaces and that is not absorbed. Therefore, surface reflectance properties are important optical attributes of a material.

Acquiring realistic reflectance properties of real-world objects, such as their spatially varying colors, specularities, roughnesses, translucencies, and diffuse reflectances, can be quite difficult, however. The image acquired from an object generally depends not only on its characteristic reflectance properties, but also on the conditions of illumination. The process of capturing the radiance of light reflected by an object from a full range of incident illumination directions can be lengthy, and can require specialized equipment. Surface reflectance properties may often be crafted laboriously by hand, using image-editing software.

To address these issues, mathematical reflectance models have been developed which parameterize an object's bidirectional reflectance distribution function (BDRF). The BDRF provides the ratio of the reflected radiance to the incident flux, per unit area, for all directions of view and incident illumination. Typically, these analytic reflectance models parameterize the BDRF in terms of the diffuse color of the object, the specular color of the object, and the specular roughness parameter of the object. This parameterization allows these models to be fitted to sparser samples of the BDRF. It can be difficult, however, to reliably estimate both the diffuse and specular components of an object's surface reflectance, using these mathematical models with a limited number of samples. In particular, parameters obtained by fitting to a limited number of samples can grossly mischaracterize the specular properties of a material.

Accordingly, there is a need for an apparatus and method that allow both the diffuse and the specular reflectance properties of an object to be estimated reliably, without requiring excessive amounts of data and/or complex equipment.

SUMMARY

A reflectometry apparatus and method is presented that uses an extended light source having an elongated configuration to illuminate an object, instead of using a point light source. Using a simple gantry to move the extended light source across an object, the light source can be made to provide illumination on an object from a full range of directions of incident illumination. The data set resulting from images acquired as light from the light source sweeps across a surface of the object provides information that is sufficient to reliably estimate both the diffuse and specular reflectance properties of the object.

A reflectometry apparatus in accordance with one embodiment includes a light source adapted to generate light that illuminates at least a portion of a surface of an object. The light source has an elongated configuration and extends from one end to another end. For example, the light source may be a linear, cylindrical neon tube. In one embodiment, the apparatus includes an actuator configured to move the light source along a trajectory during a time period so that light from the light source sweeps across the surface of the object during the time period. Alternatively, the light source may be moved manually by an operator. The apparatus includes a camera configured to receive, during this time period, light reflected from the surface, and to generate therefrom image data representative of a plurality of images of the object surface.

The apparatus includes a data processor configured to process the image data from the camera, so that spatially varying surface reflectance parameters of the object can be determined for each point on the surface of the object. These reflectance parameters may include the diffuse reflectance parameter, the specular reflectance parameter, and the specular roughness parameter. A reflectance trace table is synthesized for a range of model parameters using a virtualized rendition of the linear light source. For each pixel, the observed reflectances are compared to the synthesized reflectance trace table, to determine the reflectance parameters that most closely match the observed data. A variation in surface normals and surface heights can also be reliably measured, for non-flat surfaces. The translucency parameter can also be measured using the above-described apparatus.

BRIEF DESCRIPTION OF THE DRAWINGS

FIGS. 2A, 2B, 2C, and 2D illustrate the measured reflectance traces for different materials.

FIGS. 4A, 4B, 4C, and 4D illustrate the fitting of data to a parameterized reflectance model, using a pre-computed table of synthesized reflectance traces.

FIG. 5 illustrates the use of laser stripe scanning to measure the variations in surface geometry of an object.

FIGS. 6A and 6B illustrate the measurement of the translucency parameter $\rho_{trans}$ of an object surface.

DETAILED DESCRIPTION

An apparatus and method is presented that reliably measures both the diffuse and the specular reflectance parameters of an object, as well as its translucency and the variation in its surface geometry, by detecting light reflected from the object surface while an extended elongated light source is moved over the object surface.

Figure 1:
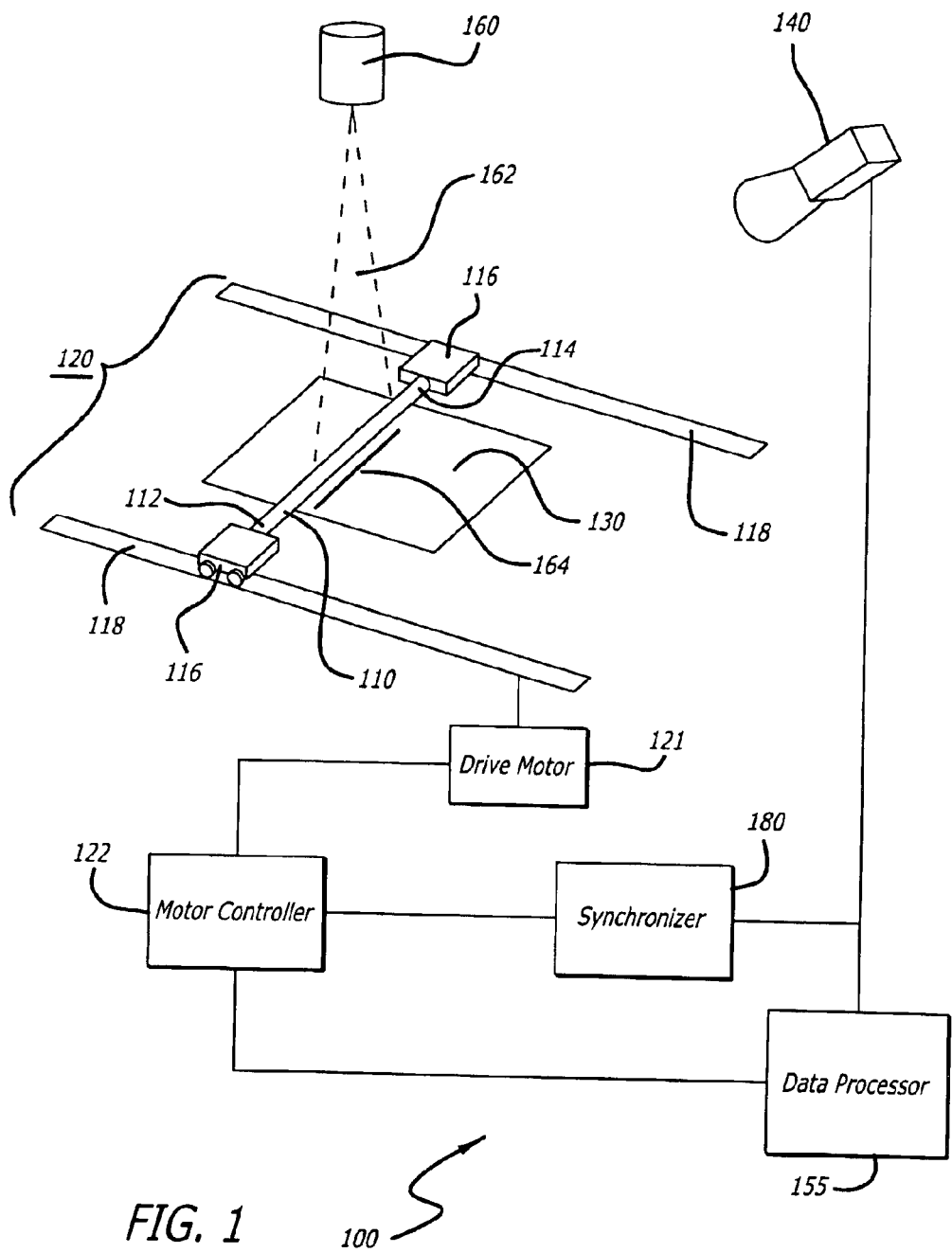
FIG. 1 is a schematic block diagram of a reflectometry apparatus in accordance with one embodiment.

FIG. 1 is a schematic block diagram of a reflectometry apparatus 100, configured to measure the surface reflectance properties of an object 130, in accordance with one embodiment. The reflectometry apparatus 100 has an extended, elongated light source 110 that is moved across the surface of an object 130 along a one-dimensional trajectory, instead of having a point light source that needs to be moved across the full two-dimensional hemisphere of incident illumination directions. The light source 110 has an elongated configuration extending from one end 112 to another end 114. In this section, a linear light source will be described that has a substantially cylindrical configuration, and that is moved translationally. It should be noted, however, that the apparatus and method of the present invention is not limited to a linear light source that is moved translationally along a substantially straight trajectory, and that any other type of elongated light source that extends from one end to another can be used. For example, an extended light source may be used that has a curvilinear or an arcuate configuration, or that has a wavy or sinusoidal configuration. Such extended light sources may be moved rotationally, or may be moved along a curvilinear or an arcuate trajectory.

In overview, the apparatus 100 includes a linear, elongated light source 110; an actuator 120 that moves the light source 110 across over the surface of the sample object 130, whose surface reflectance properties are being measured; an optical imaging system 140 that acquires a series of images as the light from the light source 110 moves across the object 130; and a data processor 155 that processes the image data generated by the optical imaging system 140 so that the surface reflectance properties of the object 130 can be determined. A light box (not shown) or other area illumination source may be provided behind the object 130 and illuminated before or after the light source is moved. The light source 110 is moved in such a way that light from the light source 110 sweeps across and illuminates the entire surface of the object 130 during a single pass of the light source 110 over the object 130. In the embodiment illustrated in FIG. 1, the object 130 is shown as having a flat surface; however, objects having any kind of non-flat configuration can be used as the sample object. Objects having non-flat surfaces are described in paragraphs.

The optical imaging system 140 generates a series of images of the object while the light source 110 is moved over the object 130. The optical imaging system 140 may, in one embodiment, be placed at a single viewing direction with respect to the object throughout the motion of the light source 110. The apparatus 100 may include a laser 160 that forms a laser stripe scanner, together with the optical imaging system 140 and the actuator 120. Surface geometry variations of the object 130 can be recorded using the laser stripe technique. The apparatus 100 may also include a translucency measurement system (not shown) that measures the translucency parameter $\rho_{trans}$.

In the embodiment shown in FIG. 1, the light source 110 device is a white neon tube, and has a linear and substantially cylindrical configuration. As mentioned earlier, any other type of extended and elongated light source may also be used. A neon tube has a lower flicker and whiter spectrum, compared to a fluorescent tube, and a lower heat output compared to an incandescent light. The neon tube may, by way of example, be about 1 cm in diameter and about 50 cm long, although light sources having any other dimensions may also be used.

In the embodiment shown in FIG. 1, the actuator 120 is a simple translational gantry that moves the linear light source 110 along a one-dimensional rectilinear trajectory, whose direction is shown in FIG. 1 by an arrow. As mentioned previously, however, any other type of actuator or motion platform can be used, including but not limited to a rotational gantry, and to actuators configured to impart motion to the light source 110 along a curvilinear or an arcuate trajectory, or to being moved manually in a hand-held manner by an operator. The translation gantry 120 shown in the illustrated embodiment is configured to move the linear light source 110 horizontally across over the surface of the object 130, at a fixed distance h. In one form, the light source 110 may be mounted at the ends 112 and 114 to two trolleys 116 whose grooved wheels ride along two L-beams or rails 118. A drive motor 121, controlled by a motor controller 122, may drive the motion of the gantry.

The optical imaging system 140 is a digital camera in the illustrated embodiment, although any other type of optical imaging system may be used. In one embodiment, the camera 140 captures high resolution photographs every few seconds from a single viewing angle with respect to the object 130, while the light source 110 is moved across the object 130 during a time period. In other embodiments of the invention, the camera 140 may be positioned at two or more viewing angles with respect to the object 130, and the light source 110 may effect two or more passes across the object. As known in the art, an image captured by a digital camera is formed of a plurality of pixels (typically a two-dimensional array of pixels), where the pixel value of a given pixel represents the image brightness of a unit area on the surface corresponding to that pixel. The photographs may have a resolution of about 3072×2048 pixels, by way of example, although a camera 140 having any other resolution can be used. The optical imaging system 140 may acquire images with three spectral sensitivity channels corresponding to reflectance in the red, green, and blue areas of the spectrum, although a system having additional spectral channels within or outside of the visible spectrum could also be used.

The apparatus 100 may include a synchronizer 180 that allows the photographs to be generated and the gantry trolleys translated in a synchronized manner. For example, the synchronizer may include a processor containing software created using the control API of the camera 140, and the API of the gantry 120. Upon synchronization, a photograph may be taken, for example, for every millimeter of incremental motion of the light source 110, for example. Typically, the time period in which the motion of the light source 110 takes place may be about 30 seconds to about 30 minutes, depending on the speed of the image capture, and a few hundred images are captured during this time.

The laser 160 forms, together with the camera and the gantry, a laser scanning system or a laser stripe profiler. The laser 160 emits a plane of laser light 162, which forms an illuminated stripe 164 on the surface of the object 130. The illuminated stripe is viewed by the camera 140, which is disposed at a distance from the laser plane 162. As the light source 110 is moved, the laser stripe 164 is also scanned throughout the surface of the object 130. In one embodiment, the laser 160 is a miniature structured light diode laser, having a 60 degree line lens mounted to project the laser stripe parallel to and about 38 mm behind the linear light source 110. Surface variations cause deformations in the stripe, as seen from the camera 140. These deformations can be used to recover variations in the geometric structure of the object 130.

The data processor 155 is configured to process the image data, generated by the camera 140 as a series of photographs of the illuminated object 130 is taken, so that the surface reflectance parameters can be determined for every point on the surface of the object 130. As is well known, reflectance is defined as the ratio of the energy of reflected light to the energy of the incident light. As known, surface reflectance can be described in terms of two components, namely diffuse reflectance and specular reflectance. Diffuse (or "Lambertian") reflection occurs when light is scattered substantially equally in all directions as it reflects from the object surface. A perfectly Lambertian surface that is subject to uniform illumination has a fixed radiance regardless of its orientation. Specular reflection occurs when light is reflected substantially in the "mirror direction," which means that the angle of reflection is substantially equal to the angle of incidence, or distributed thereabout. Specular reflection thus leads to a glossy or mirror-like appearance.

Diffuse reflection is characterized by a single parameter per color channel, namely the diffuse reflectance parameter $\rho_d$ that is representative of the proportion of incident light that undergoes diffuse reflection. On the other hand, there are two parameters per color channel associated with specular reflection, namely the specular reflectance parameter $\rho_s$ and the specular roughness parameter $\alpha$. The specular reflectance parameter $\rho_s$ represents the proportion of incoming light that undergoes specular reflection. Materials such as soot or chalk have small values of $\rho_s$, while materials that have glossy surfaces, such as glass and polished metal, have larger values of $\rho_s$. The specular roughness parameter $\alpha$ is indicative of the microscopic roughness of the surface. Larger values of $\alpha$ lead to a spreading or blurring of the specular reflection, i.e. are characteristic of rough, unpolished surfaces that provide a blurred specular reflection, while smaller values of $\alpha$ are characteristic of smooth, polished surfaces that provide a sharp, un-blurred specular reflection.

Because of the omni-directional nature of diffuse reflection, the diffuse reflectance parameter can be observed and determined relatively easily. On the other hand, the specular reflectance parameters are harder to observe and estimate, since specular reflection can only be observed within a limited range of viewing angles with respect to an illumination direction. For these reasons, it can be very difficult to reliably estimate both the diffuse and specular reflectance parameters of an object surface, as explained previously in the background section of this application. By using an elongated and extended light source, rather than a point light source, the apparatus 100 allows both the diffuse and the specular reflectance parameters of an object surface to be estimated reliably, as described more fully in this section.

To capture a data set using the apparatus 100, the object 130 is placed on a light box (not shown) between the two rails 118. On either side of the object 130, calibration strips (not shown) may be placed, the strips consisting of diffuse and sharp specular materials. In order to measure the light reflection at a specific point P on the object surface, the surface point P must be observable from the camera position, and light from the light source 110 must illuminate the surface point P. The camera 140 may be placed on a tripod, looking down at the object 130 at an appropriate angle of incidence from perpendicular to the object 130. The angle of incidence should be chosen so that the observed position of the diffuse and specular peaks are adequately separated, without unduly foreshortening the object's appearance in the camera 140. In one embodiment, the angle of incidence may be approximately 55 degrees from perpendicular, although the camera 140 may be placed at other angles of incidence.

The light source 110 is then attached to the gantry 120, and the light source 110 is turned on. The laser 160 is also turned on, so that a plane 162 of laser light is projected onto the light source 110. The gantry drive motor 121 is then activated so that the light source 110 undergoes translational motion, during a time period. Once the gantry 120 starts moving, the time lapse shutter release on the camera 140 is released so that a photograph of the object 130 is taken at each one of a plurality of N time points $t_i$ (i=1, . . . , N) within the time period of motion of the light source 110, as the light source 110 moves across the object 130. The result is that N photographs are generated by the end of the time period of motion. For example, a photograph may be taken every few seconds as the light source 110 moves through the object 130. The control software in the synchronizer 180 then alternates between translating the gantry and taking photographs of the object. The recording is stopped when the laser stripe of the light source has moved past the final edge of the object 130. Typically, this may take from approximately 30 seconds to 30 minutes, depending on the speed of the image capture, although the process may be carried out even more quickly if necessary (for example a fraction of a second) in embodiments in which the speed of image capture is ultra-fast.

The image data generated by the camera 140 are processed by the data processor 155. Each digital image or photograph is represented by a 2D array of pixels. The camera's position, orientation, and focal length are derived, so that the image coordinates (i.e. the coordinates of the pixels) can be correctly related to the coordinates of the corresponding points on the surface of the object. Using well known methods, for example known photogrammetric modeling techniques, a projection function may be constructed that projects image coordinates to their corresponding 3D location P on the surface of the object as determined in an x-z planar coordinate system.

The image data may be represented as $I_{u,v}(t)$, where t ranges from $t_i$ to $t_N$ (N being the number of images generated during a single pass of the light source over the object), (u,v) refers to the coordinates of a pixel in the 2D array, and $I_{u,v}(t)$ provides a graph of the pixel's intensity as the light source 110 moves over the corresponding point on the object's surface. Such a graph is referred to in this application as the reflectance trace of a pixel. The reflectance trace of a pixel is indicative of the observed intensity, at each time point ti (I=1, . . . , N) of the light reflected from a point on the object surface that corresponds to that pixel.

FIGS. 2A, 2B, 2C, and 2D illustrate the measured reflectance traces for a variety of materials. FIG. 2A shows the reflectance trace for diffuse vellum. FIG. 2B shows the reflectance trace for shiny black paper. FIG. 2C shows the reflectance trace for gold. FIG. 2D shows the reflectance trace for blue decal. The reflectance parameters $\rho_d$, $\rho_s$, and $\alpha$ can be determined with respect to each color channel (RGB, or red, blue, and green), so the diffuse color of a surface point is given by the RGB triple $(\rho_{dr}, \rho_{dg}, \rho_{db})$, and the specular color of a surface point is given by the RGB triple $(\rho_{sr}, \rho_{sg}, \rho_{sb})$, In the graphs shown in FIGS. 2A–2D, the red color channel is shown as a solid curve; the blue color channel is shown as a dashed curve; and the green color channel is shown as a dotted curve.

In a reflectance trace, a peak corresponding to the specular reflection of the pixel typically appears first, followed by a broader peak corresponding to the diffuse peak of the pixel, followed by a red spike corresponding to the time at which the laser stripe passes over the surface point corresponding to the pixel. This is shown in the reflectance traces plotted in FIGS. 2A–2D. As the light moves across the object, the specular lobe reflection appears first near the time $t_m$ at which the light source is at a mirror angle with respect to the camera, followed by the diffuse reflection at time $t_d$ when the light passes directly above the surface point.

As seen from FIG. 2A, diffuse materials such as diffuse vellum may not exhibit a significant peak corresponding to the specular lobe expected at time $t_m$. As seen from FIGS. 2B and 2C, relatively glossy materials such as shiny black paper (shown in FIG. 2B) and gold (shown in FIG. 2C) may not exhibit a significant peak corresponding to the diffuse lobe expected at time $t_d$. As shown in FIG. 2D, materials such as blue decal exhibit both a relatively broad specular lobe and a relatively broad diffuse lobe. For diffuse vellum (shown in FIG. 2A) and for gold (shown in FIG. 2C), a peak corresponding to the laser stripe, used to determine the surface point's height, is visible at the right.

To determine the reflectance parameters $\rho_s$, $\rho_d$, and $\alpha$ from the measured reflectance traces, a parameterized model fitting technique is implemented by the data processor 155. The data processor 155 first computes a table of synthesized reflectance traces. This table shows how the diffuse and specular reflectance lobes would appear under a virtualized version of the moving light source, for a variety of model reflectance parameters forming a predetermined set. Then, for each pixel, the measured or observed reflectance trace (i.e. the series of intensity values for each time point $t_i$ at which the images were captured) with the tabulated synthesized reflectance lobes, to determine which reflectance model parameters most closely produce the observed reflectance values.

The data processor 155 may include a computer-readable medium having stored therein computer-readable instructions for a processor. These instructions, when read and implemented by the processor, cause the processor to input and store the image data received from the camera, and to implement the steps described in the previous paragraph, namely: 1) measure a reflectance trace for each pixel, wherein the reflectance trace indicates the recorded intensities at each time point $t_i$ (i=1, . . . N) of light reflected from a surface point corresponding to the pixel; 2) compute for a table of synthesized reflectance traces, each synthesized reflectance trace being indicative of the intensity, at each time point, of light originating from a virtualized rendition of the light source and reflected from a surface point that corresponds to the pixel, and each synthesized reflectance trace being computed using one of a predetermined set of model surface reflectance parameters; and 3) compare, for each pixel, the measured reflectance trace to the table of synthesized reflectance traces, so as to determine the surface reflectance parameters that best fit the measured reflectance trace. The computer-readable medium may be any medium known in the art, including but not limited to hard disks, floppy diskettes, CD-ROMs, flash memory, and optical storage devices. The computer readable instructions discussed above may be provided through software that is distributed through the Internet.

This reflectance model fitting procedure requires that the line equation I(t) for the position of the moving linear light source be known, for each image I(t). The data processor 155 obtains the line equation by first determining the time-varying position of the laser stripe $\hat{l}(t)$. This is done by marking the line of the laser stripe's intersection with the xz plane in each of two images in the image sequence, one at $t_a$ when the laser is near the top of the frame and one at $t_b$ where the laser is near the bottom of the frame. Each image-space line is then projected onto the xz plane in object space, to compute $\hat{l}(t_a)$ and $\hat{l}(t_b)$. All other values of $\hat{l}(t)$ are linearly interpolated, based on the values at $t_a$ and $t_b$. Since the light source 110 is at a height h and at a fixed distance d in front of the laser 160, the position of the light source is given by $$I(t)=\hat{l}(t)+(d \sin \beta, h, d \cos \beta), \quad (1)$$

where $\beta$ is the angle at which the light source is mounted, with respect to the direction of the gantry motion.

Using equation (1) for I(t), which provides the position of the linear light source as a function of time, the time $t_d$ at which the light source is directly above the surface point, and the time $t_m$ at which the light source is at a mirror angle to the surface with respect to the camera can be computed for any surface point P. Generally, $t_m$ lies near the specular peak and $t_d$ is situated near the diffuse peak.

Figure 3:
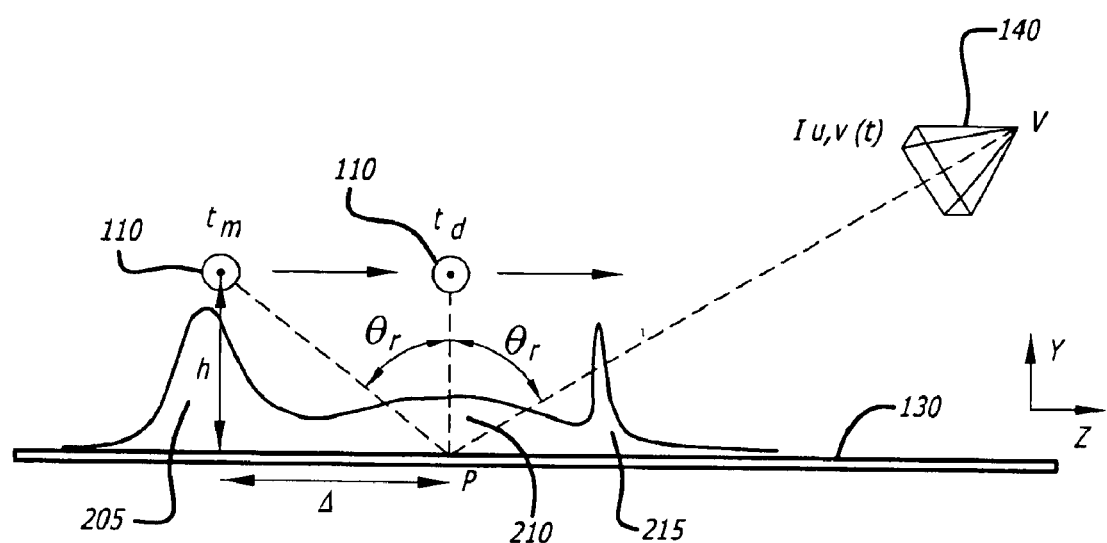
FIG. 3 illustrates the registration of data representative of a reflectance trace, as the light source is moved across the object surface.

FIG. 3 illustrates the registration of data representative of a reflectance trace, as the light source 110 is moved across the object surface. The arrows in FIG. 3 indicate the motion of the light source 110, for which a cross-sectional view is illustrated in the figure. For each pixel having coordinates (u,v) in the image plane and corresponding to a surface point P, the 3D position and orientation of the camera and a model of the movement of the light source is used to determine the time $t_d$ when the light source is directly above the surface point P, and the time $t_m$ when the light source is at a mirror angle ($\theta_r$) to the surface with respect to the camera. In FIG. 3, the reflectance trace in the background shows the amount of light reflected by the surface point P on the object surface toward the camera 140, as the light source 110 moves across the object surface. The shape of the reflectance trace shows a specular peak 205 and a diffuse peak 210 at the corresponding time points $t_m$ and $t_d$, as well as a laser stripe peak. Also shown in FIG. 3 is $\Delta = t_d - t_m$, which is used to delimit the region in which a reflectance trace is analyzed up to the area $t_m \pm \Delta$.

A specific analytic reflectance model can be used in this model fitting technique, to fit the data observed with the apparatus 100. In particular, the isotropic Gaussian lobe model developed by Ward is used in this section to describe reflectance model fitting. The Ward model is used because of its combination of simplicity and physical accuracy; however the reflectometry apparatus and method described in this section can be used with any other mathematical models as well, with very satisfactory results.

The Ward model specifies that a surface point P will reflect light from a direction ($\theta_i, \phi_i$) to a direction ($\theta_r, \phi_r$) with the following distribution function $f_r$:

$$f_r(\theta_i, \phi_i; \theta_r, \phi_r) = \frac{\rho_d}{\pi} + \rho_s \cdot \frac{1}{\sqrt{\cos \theta_i \cos \theta_r}} \cdot \frac{\exp[-\tan^2 \delta / \alpha^2]}{4\pi \alpha^2} \quad (2)$$

In the distribution function given in equation (2) above, $\delta$ is the angle between the surface normal $\hat{n}$ at surface point P, and the half vector $\hat{h}$ between the incident and reflected directions. As explained earlier, the reflectance parameters $\rho_d$, $\rho_s$, and $\alpha$ may be determined with respect to each color channel (RGB, or red, blue, and green). The specular color ($\rho_{dr}, \rho_{dg}, \rho_{db}$) of a surface point P is usually spectrally even for dielectric materials such as plastic, and has a particular hue in the case of metals such as gold and bronze. Usually, the same $\alpha$ (roughness) parameter can be used for all color channels.

In one embodiment, the data processor 155 is configured to estimate $\alpha$ based on a weighted average of the three color channels. The data processor 155 can be configured to analyze the image data to estimate ($\rho_d, \rho_s, \alpha$) for every point on the object surface, as described further below. Additionally, a surface normal $\hat{n}$ and a displacement d can be recovered for each surface point using laser stripe scanning, as described in paragraphs. Further, the translucency $\rho_{trans}$ of each surface point can also be estimated. In sum, a parameter vector ($\rho_d, \rho_s, \rho_{trans}, \hat{n}, d$) can be reliably determined for every point on the object surface, using the apparatus 100.

A discrepancy results in this model fitting process, because the distribution function $f_r$ in the Ward reflectance model specifies reflected light for each specific incident angle of illumination, whereas the reflectance measurements $I_{u,v}(t)$ by the apparatus 100 result from light reflected from an entire area of incident illumination, namely the cylindrical linear light source 110. To address this discrepancy, a virtual version of the linear light source 110 is created by the data processor 155. The predicted appearance of its reflected light is calculated in advance, for a variety of diffuse and specular parameters that form a predetermined set. In other words, the data processor 155 generates a pre-computed table of synthesized (or rendered) reflectance traces. The data processor 155 then compares the statistical characteristics of the synthesized reflectance traces to the statistical characteristics of a real pixel's reflectance trace that is actually observed and measured, in order to determine which reflectance model parameters best correspond to the observed data.

With respect to the diffuse and specular parameters, the model fitting process is described in this section for the case of flat surfaces, not taking into account any variations in surface normal and surface height. The data processor 155 registers the observed or measured reflectance traces into a common coordinate space. The appropriate table of pre-synthesized or pre-rendered reflectance traces, to be fit to the data, is then computed. Finally, the diffuse and specular parameters of each surface point is determined by comparing the statistics of the real data to the rendered or synthesized basis data.

In particular, the data fitting process is one of finding those values of $\rho_d$, $\rho_s$ and $\alpha$ such that for each pixel the following equation is satisfied:

$$I(t) = \rho_d D(t) + \rho_s S_\alpha(t) \tag{3}$$

In equation (2) above, $I(t)$ represents the total observed reflectance intensity, $D(t)$ represents the diffuse reflectance intensity, and $S_\alpha(t)$ represents the specular reflectance intensity at a roughness parameter $\alpha$. All intensities are expressed as a function of time $t$, where $t$ ranges from $t_1$ to $t_N$ as the light source effects a single pass over the object.

It is important that the reflectance function $f_r$ be specified in terms of light from an extended elongated light source rather than in terms of light from a point light direction at $(\theta_i, \phi_i)$. Accordingly, in one embodiment, the data processor 155 is configured to numerically integrate the distribution function $f_r$ across the light source surface for a range of surface roughness parameters $\alpha$ and of light source positions relative to the pixel. In one embodiment, the integrations are carried out under the assumption that the viewing direction $(\theta_r, \phi_r)$ is perpendicular to the linear light source, i.e. that $\phi_r = 0$ and $\theta_r$ is constant.

In one embodiment, the data processor 155 stores the results of the tabulations of synthesized reflectance traces in a series of functions $S_\alpha(t)$, which correspond to the height of a specular lobe with $\rho_s = 1$ for a range of light source positions. In one embodiment, the parameterization of $t$ is chosen so that at $t = 0$, the light source is directly above the surface point, and that at $t = 1$ the light source is at the mirror angle with respect to the surface point and the viewing direction. The function $D(t)$, which corresponds to the height of a diffuse lobe with $\rho_d = 1$ for the same range of light positions, is also computed.

In one embodiment, the linear light is rendered or virtualized as a cylindrical light having a diameter equal to the diameter of the actual linear light source 110. In this way, the sharp specular peaks are made to match accordingly. To render or virtualize the cylindrical light, the light is uniformly sampled, transversely and radially. The specular fitting process can be speeded up by computing the mean $\mu$ and the standard deviation $\alpha$ of the shape of each specular lobe in the table. These numbers $\mu$ and $\alpha$ characterize the position and breadth of the specular lobe as produced by the linear light source.

In one embodiment, the data processor 155 is configured to first fit the diffuse lobe of the linear light reflectance trace, thereby determining the $\rho_d$ parameter for each color channel. Because it is assumed that every surface point P has a vertical surface normal (i.e. that the object surface is flat), the diffuse peak is expected to occur at a time $t_d$ when the light is directly above the surface point. The specular peak is assumed to be at a sufficient distance away from the diffuse peak so that its contribution to the reflectance trace is negligible at $t_d$. The height the height of diffuse peak $I_d$ is measured as the height of the reflectance trace at $t_d$. In one embodiment, the amount of light falling on a pixel (u, v) is determined by including a strip of diffuse material of known reflectance $\rho_{standard}$ along the sides of the object. The height of the diffuse peak $I_{standard}$ is measured for pixels on this known sample. $\rho_d$ is then computed using the following equation:

$$\rho_d = I_d \cdot \frac{\rho_{standard}}{I_{standard}} \tag{4}$$

where $I_{standard}/\rho_{standard}$ is a measurement of the irradiance at the object surface.

Once $\rho_d$ is calculated, the data processor 155 proceeds to determine the specular reflectance parameters of the sample surface point. Since the diffuse lobe is broad, its contribution cannot be assumed to be negligible in the region of the specular peak. Accordingly, the data processor 155 subtracts the contribution of the synthesized diffuse lobe from the reflectance trace, before fitting the specular peak.

FIGS. 4A, 4B, 4C, and 4D illustrate the fitting of observed data to a parameterized reflectance model, using a table of pre-computed synthesized reflectance traces. FIG. 4A shows the original reflectance trace of the sample object 130. FIG. 4B illustrates the fitting of the diffuse lobe, i.e. a $\rho_d$ is chosen such that $\rho_d D(t)$ matches the height of the diffuse peak. FIG. 4C illustrates the subtracting of the diffuse peak. In FIG. 4C, the fitted diffuse peak is subtracted from the reflectance trace to isolate the specular peak.

Once the diffuse lobe is subtracted, the specular lobe is examined independently. FIG. 4D illustrates the fitting of the specular peak. Specular peaks generally lie near the mirror angle $t_m$, and further away from $t_d$. In the embodiment illustrated in FIG. 4D, the data processor 155 computes the standard deviation $\sigma$ of the specular peak, and uses $\sigma$ to choose the appropriate specular roughness parameter $\alpha$. The specular reflectance parameter $\rho_s$ is determined as the ratio of the total energy of the specular peak compared to the energy of the specular sample $S_\alpha(t)$ in the reflectance table to produce the modeled or synthesized specular peak in FIG. 4D.

Specifically, the data processor 155 characterizes the specular peak in terms of its mean $\mu$, standard deviation $\sigma$, and total energy $I_{avg}$ as follows:

$$\mu = v \frac{\sum t \cdot \hat{I}(t)}{\sum \hat{I}(t)} \tag{5}$$

-continued $$\sigma^2 = v\frac{\sum (t-\mu)^2 \hat{I}(t)}{\sum \hat{I}(t)} \quad (6)$$

$$S = v\sum \hat{I}(t) \quad (7)$$

In one embodiment, the limits of the summations in the above equations (5)–(7) are made to range from $t_m-\Delta$ to $t_m+\Delta$. This means that the region of $\hat{I}(t)$ that is considered lies in the neighborhood of $t_m$, with a radius equal to the distance between $t_d$ and $t_m$. All values may be normalized using a scaling factor $v=1/(2\Delta)$, in order to account for the differences in widths for different pixels due to slight perspective effects in the camera.

The data processor 155 then searches the synthesized reflectance trace table, in order to find a specular peak having the same standard deviation $\sigma$ as that observed in the actual specular peak. The $\alpha$ value that produced that specular peak is then chosen to be the specular roughness parameter of the pixel. To determine the desired specular reflectance parameter $\rho_s$, the ratio of the lobe's sum S to the sum of the specular lobe with the roughness parameter $\alpha$ in the table, is computed. This ratio is scaled with the same scaling factor as used for the diffuse component, as seen in the equations above.

The technique described above assumes that the object surface is flat. If the object has surface normal variations, i.e. a non-flat surface, the surface reflects light differently. A surface normal map can be recovered using the apparatus 100, by effecting two passes of the linear light source over the object, at different diagonal angles. From these two passes it is possible to estimate variations in both components of the surface normal. For non-flat surfaces, a surface height map, i.e. an estimation of the surface displacement d, can also be recovered, using the laser stripe system. The surface height map can be used to tune the $t_d$ and $t_m$ values for each pixel, as well as to provide a displaced surface for rendering.

FIG. 5 illustrates the use of laser stripe scanning to measure the variations in surface geometry of an object. Variations in the surface height change the temporal location of the mirror angle, so in order to maintain registration a laser stripe 164 is attached to the linear light source 110 to measure the surface shape of the object 130 (now shown with a bumpy, non-flat surface). The laser 160 (see FIG. 1) produces a red laser stripe 164 which projects a vertical plane of light 162 (see FIG. 1) onto the object 130, about 38 mm behind the light source 110. For each pixel (u,v), the time at which the laser stripe crosses the corresponding point on the object is detected, by locating the pixel $I_{u,v}(t)$ which has the brightest red component. Intersecting the camera ray VP with the plane of the laser at the time the laser stripe 164 crosses pixel (u, v) yields point Q on the surface. To obtain the point P on the object surface corresponding to the pixel image coordinate (u,v), the camera ray corresponding to the pixel is intersected with the plane of the laser to obtain the surface point P, as illustrated in FIG. 5. The appropriate $t_d$ and $t_m$ values for point P can then be computed as described earlier. The displacement map is used to adjust the mirror angle position $t_m$ for the raised surfaces, as well as to provide a geometric model of the object.

To estimate the variations in surface normal, the object is scanned twice, with the light source in two different positions. For example, in one embodiment the light source may be positioned at two diagonally opposite viewing angles with respect to the camera. If a pixel's surface normal $\hat{n}$ points toward the approaching light, its specular peak occurs earlier in I(t), and if the surface normal points away from the approaching linear light source, its specular peak occurs later. The two light source directions thus allow both components of the surface normal to be estimated.

To determine how specular peaks respond to changes in surface normal, in one embodiment, four different reflectance tables are rendered, for a $\beta=15°$ degree diagonal light source. In this embodiment, the first two reflectance tables are rendered with the surface normal set to $\pm\delta$ degrees rotated about the z axis (yielding a perturbation in the x component) and the second two tables $\pm\delta$ degrees about the x axis (yielding a perturbation in the z component). For each reflectance table, the $S_\alpha$ lobe is located that has the same standard deviation $\sigma$ as the pixel's observed specular lobe in $\hat{I}(t)$. The corresponding means $\mu_{x-},\mu_{x+},\mu_{z-},\mu_{z+}$ of each of these lobes are then found. These four means are used to produce a bilinear function $f_{+15}(\Delta x,\Delta z)$ mapping the normal perturbation to the means.

By symmetry, a similar function $f_{-15}(\Delta x,\Delta z)$ is constructed for $\beta=-15°$ in this embodiment, by simply swapping the values of $\mu_{x-}$ and $\mu_{x+}$. For the pixel that is being considered, the data processor solves for the normal perturbation components $\Delta x$ and $\Delta z$, by equating $f_{+15}(\Delta x,\Delta z)$ and $f_{-15}(\Delta x,\Delta z)$ to the pixel's actual measured means for the two runs, namely $\mu_{+15}$ and $\mu_{-15}$. This yields a 2×2 linear system of equations, as follows:

$$\mu_{+15} = \mu_{x-} + \frac{\Delta x+\delta}{2\delta}(\mu_{x+}-\mu_{x-}) + \frac{\Delta z}{2\delta}(\mu_{z+}-\mu_{z-}) \quad (8)$$

$$\mu_{-15} = \mu_{x+} + \frac{\Delta x+\delta}{2\delta}(\mu_{x-}-\mu_{x+}) + \frac{\Delta z}{2\delta}(\mu_{z+}-\mu_{z-}) \quad (9)$$

Because the above-described technique for computing surface normals depends on analyzing specular reflection, it works relatively well on specular surfaces and relatively poorly on diffuse surfaces. For this reason, in one embodiment the final surface normal map is produced by combining the surface normals estimated by specular reflection with surface normals obtained by differentiating the laser-scanned displacement map d. Once a surface normal has been estimated for each pixel, the diffuse and specular parameters may be re-estimated, based on the improved knowledge of the surface characteristics.

In one embodiment, the diffuse and specular parameters are re-estimated by adjusting the model of the diffuse lobe to be rendered with based on the new and improved determination of the surface normals. In this embodiment, a 20×20 table of diffuse lobes D'x,z(t) is pre-computed, for surface normals varying in x and z, and bilinear interpolation is used to create a D'(t) for the particular surface normal. From this table, $\rho_d$ is re-computed, and a new specular reflectance trace $\hat{I}'(t)=I(t)-D'(t)$ is then produced. From this new reflectance trace, a new $S_\alpha(t)$ is fitted, thereby obtaining new parameters $\rho_s$ and $\alpha$. One iteration of this procedure was found to significantly increase the consistency of the specular roughness parameters.

In the embodiment described with reference to FIG. 5, a technique has been described in which the variations in the surface normals and surface heights of the object (i.e. the 3D surface geometry of the object) is obtained by using the laser stripe at the same time the surface reflectance parameters $\rho_d$, $\rho_s$, and $\alpha$ are being measured. In other embodiments, the 3D surface geometry of the object may be recovered using alternative techniques, either before or after the capturing of the surface reflectance data. These alternative techniques include, but are not limited to, the following: 1) physical measurement of the surface geometry variations; 2) structured illumination; and 3) forms of laser scanning other than the laser stripe technique. Alternatively, the surface geometry may not need to be estimated at all in cases in which the object has a known geometry, for example has a completely flat surface.

In the embodiments described in paragraphs above, an isotropic reflection model has been described, and methods have been described in which up to two passes of the light source are made over the object, from two different directions (for example from two diagonal directions). In alternative embodiments, non-isotropic reflectance models may be used, in order to recover anisotropic reflectance properties, which are exhibited for example by brushed metal or by cloth fibers. In these embodiments, three or more passes of the extended elongated light source may be made over the object.

FIGS. 6A and 6B illustrate the measurement of the translucency parameter $\rho_{trans}$ using the apparatus 100, in accordance with one embodiment. Thin objects such as manuscripts can be translucent, which means that they transmit light through the front when lit from behind. The data processor solves for this translucency component $\rho_{trans}$ by taking one additional image $I_{backlit}$ of the object 130, as illuminated from behind by a light box 190, as well as an image $I_{lightbox}$ of the light box 190 with the object 130 removed. A set of two such images are shown in FIGS. 6A and 6B.

To determine the amount of transmitted light for each pixel of each color channel, in one embodiment, the data processor computes $\rho_{trans}=I_{backlit}/I_{lightbox}$, to obtain the percentage of light transmitted at each pixel. In the reflectance model used in this procedure, it is assumed that any light transmitted through the material becomes diffused, so $\rho_{trans}$ is not measured for different incident and outgoing directions. This is a simplified model of translucency, and the simplified model was found to approximate the scattering characteristics of the object with sufficient precision.

In sum, the reflectometry apparatus and method described above used an extended and elongated light source, to produce a data set that supplies sufficient information to reliably and independently estimate the material's diffuse and specular reflectance properties, without having to independently observe all the different illumination directions. Using a linear, extended light source for reflectometry provides a number of advantages, compared to using a point light source. For example, the light source needed to make just one pass over the object for a single viewing direction in order to have it exhibit both its diffuse and specular reflectance characteristics at each surface point. Also, the contrast ratio between the specular and diffuse peaks was found to be reduced, allowing for standard digital imaging systems to acquire the reflectance data. Further, the mechanics for moving a light source in just one dimension are simple and inexpensive to build. Accordingly, the specular and diffuse reflectance properties of an object surface, including non-flat surfaces, could be reliably estimated in a time-effective and cost-efficient manner.

While the reflectometry apparatus and method have been described and shown with reference to specific embodiments, it should be understood by those skilled in the art that various changes in form and detail may be made therein. Many other embodiments are possible.

Other embodiments are within the following claims.

What is claimed is:

1. A reflectometry apparatus, comprising:
   a light source adapted to generate light that illuminates at least a portion of a surface of an object, the light source having an elongated configuration and extending from one end to another end;
   an actuator configured to move said light source with respect to the object along a trajectory during a time period so that light from said light source sweeps across the surface of the object during the time period;
   an optical imaging system configured to receive light reflected from the surface of the object during the time period, and to generate therefrom image data representative of a plurality of N images of the surface of the object during the time period; and
   a data processor configured to determine one or more surface reflectance parameters for one or more areas of interest across the surface of the object by processing the image data, the surface reflectance parameters including at least one specular reflectance parameter.

2. A reflectometry apparatus in accordance with claim 1, wherein said one or more surface reflectance parameters comprise spatially varying surface reflectance parameters.

3. A reflectometry apparatus in accordance with claim 1, wherein said one or more surface reflectance parameters comprise at least:
   a diffuse reflectance parameter $\rho_d$ representative of the proportion of light incident on the surface that is scattered substantially omni-directionally while being reflected;
   a specular reflectance parameter $\rho_s$ representative of the proportion of light incident on the surface that is reflected substantially in a mirror direction to the angle of incidence; and
   a specular roughness parameter $\alpha$ representative of the roughness of the surface.

4. A reflectometry apparatus in accordance with claim 1, wherein each image comprises a plurality of pixels, each pixel having an associated pixel value that represents the image brightness of a corresponding surface unit area on the surface of the object; and
   wherein each image, represented by the image data, is captured at one of a succession of time points $t_i$ (i=1, . . . , N) within a time period.

5. A reflectometry apparatus in accordance with claim 4, wherein said data processor is configured to measure a reflectance trace for each pixel; and
   wherein the measured reflectance trace of a pixel is representative of the detected intensity of light at the surface unit area corresponding to the pixel, at each time point $t_i$ (i=1, . . . , N).

6. A reflectometry apparatus in accordance with claim 5, wherein said data processor is configured to compute a table of synthesized reflectance traces; and
   wherein each synthesized reflectance trace in the table is representative of the intensity recorded at each time point of light originating from a virtualized rendition of said light source and reflected from each surface unit area corresponding to each pixel, and
   wherein each synthesized reflectance trace in the table is computed using one of a predetermined set of model surface reflectance parameters.

7. A reflectometry apparatus in accordance with claim 6, wherein the predetermined set of model surface reflectance parameters are derived from a parameterized reflectance model.

8. A reflectometry apparatus in accordance with claim 7, wherein the parameterized reflectance model comprises an anisotropic reflectance model.

9. A reflectometry apparatus in accordance with claim 7, wherein the parameterized reflectance model comprises an isotropic reflectance model.

10. A reflectometry apparatus in accordance with claim 9, wherein the isotropic reflectance model comprises an isotropic Gaussian lobe model, and wherein the distribution of light reflected by a surface point from a direction $(\theta_i, \phi_i)$ to a direction $(\theta_r, \phi_r)$ in accordance with the Gaussian lobe model is given by:

$$f_r(\theta_i, \phi_i; \theta_r, \phi_r) = \frac{\rho_d}{\pi} + \rho_s \cdot \frac{1}{\sqrt{\cos\theta_i \cos\theta_r}} \cdot \frac{\exp[-\tan^2\delta/\alpha^2]}{4\pi\alpha^2}$$

where $\delta$ is an angle between the surface normal $\hat{n}$ at the surface point and a half vector $\hat{n}$ between the direction $(\theta_i, \phi_i)$ and the direction $(\theta_r, \phi_r)$ at the surface point.

11. A reflectometry apparatus in accordance with claim 6, wherein said data processor is further configured to compare the table of synthesized reflectance traces to the measured reflectance trace, for each pixel, and to thereby select from the model parameters the parameters that best match the measured reflectance trace.

12. A reflectometry apparatus in accordnce with claim 11, wherein said data processor is configured to select the parameter that best match the measured reflectance trace by finding the values of the reflectance parameters $\rho_d$, $\rho_s$, and $\alpha$ that satisfy the following relationship for each pixel:

$$I(t) = \rho_d D(t) + \rho_s S_\alpha(t),$$

where I(t) represents the total observed intensity of the reflected light;

$S_\alpha(t)$ represents the intensity of light that is reflected from one or more areas of the surface of the object that are characterized by a specular roughness $\alpha$, at an angle of reflectance that is substantially equal to the angle of incidence;

and D(t) represents the intensity of light incident on the surface of the object that is scattered substantially omni-directionally while being reflected.

13. A reflectometry apparatus in accordance with claim 1, further comprising a synchronizer configured to synchronize the motion of said light source with the generation of images by said optical imaging system.

14. A reflectometry apparatus in accordance with claim 1, further comprising a laser configured to project a plane of laser light onto at least a portion of the surface as said light source is moved along the trajectory during the time period, so that a surface height can be determined for one or more areas of interest on the surface by observing a laser stripe that appears in each of the plurality of images as a result of the projection of the laser light plane on the surface.

15. A reflectometry apparatus in accordnce with claim 4, wherein said actuator is configured to move the light source along a first trajectory during a first time period and along a second trajectory during a second time period so that light from said light source sweeps across the surface of the object during each period;

wherein said data processor is configured to determine a surface normal for each point on the surface of the object by computing a first pair and a second pair of reflectance trace tables, and to determine a perturbation of the surface normal with respect to mutually orthogonal x- and z-axes.

16. A reflectometry apparatus in accordance with claim 15, wherein the first pair of tables is computed by setting the surface normal rotated about the z-axis by equal and opposite degrees +δ and −δ, and the second pair of tables is computed by setting the surface normal rotated about the x-axis by equal and opposite degrees +δ and −δ.

17. A reflectometry apparatus in accordance with claim 1, further comprising a translucency measurement system adapted to measure a translucency parameter for the one or more areas of interest on the surface of the object, said translucency measurement system including second light source configured to illuminate at least a portion of the surface of the object from behind the object with respect to said imaging system;

wherein said optical imaging system is further configured to detect light transmitted through the object with said second light source illuminated; and wherein said data processor is further configured to compute a translucency parameter $\rho_{trans}$ for one or more areas of interest on the surface of the object based on the intensity of said transmitted light at each pixel whose corresponding surface unit area is within the one or more areas of interest.

18. A reflectometry apparatus in accordance with claim 17, wherein said second light source and said light source are the same.

19. A reflectometry apparatus in accordance with claim 1, wherein said light source comprises a linear light source having a substantially cylindrical configuration, wherein said trajectory comprises a linear trajectory, and wherein said actuator is configured to translationally move said light source.

20. A reflectometry apparatus in accordance with claim 19, wherein said light source comprises a neon tube, said actuator comprises a translation gantry, and said optical imaging system comprises a digital camera.

21. A reflectometry apparatus in accordance with claim 3, wherein each surface reflectance parameter includes a plurality of spectral sensitivity components representative of a plurality of color channels for each pixel.

22. A reflectometry apparatus in accordance with claim 1, wherein the trajectory comprises a substantially curvilinear trajectory, and wherein said actuator is configured to rotate said light source.

23. A reflectometry apparatus in accordance with claim 1, wherein said light source has a substantially curvilinear configuration.

24. A reflectometry apparatus, comprising:

a light source adapted to generate light that illuminates at least a portion of a surface of an object, said light source having an elongatd configuration and extending from one end to another end;

wherein said light source and the object are adapted to be moved relative to each other during a time period so that light from said light source sweeps across the surface of the object during the time period;

an optical imaging system configured to receive light reflected from the surface of the object during the time period, and to generate therefrom image data representative of a plurality of N images of the surface of the object during the time period; and a data processor configured to process the image data so as to determine one or more surface reflectance parameters for one or more areas of interest across the surface of the object, the surface reflectance parameters including at least one specular reflectance parameter.

25. A reflectometry apparatus in accordance with claim 24, wherein the light source is adapted to be moved manually by an opertor during the time period.

26. A reflectometry apparatus in accordance with claim 24, further comprising:
an actuator configured to create a relative motion said light source and the object along a trajectory during the time period so that light from said light source sweeps across and illuminates the surface of the object during the time period.

27. A reflectometry apparatus, comprising:
a light source adapted to generate light that illuminates at least a portion of a surface of an object, said light source having an elongated configuration and extending from one end to another end, said light source and the object being adapted to be moved relative to each other during a time period so that light from said light source sweeps across the surface of the object during the time period; and
an optical imaging system configured to receive light reflected from the surface of the object during the time period, and to generate from the received light image data representative of a plurality of N images of the surface of the object during the time period;
wherein the image data are adapted to be processed by a data processor that is configured to determine one or more surface reflectance parameters for one or more areas of interest within the surface of the object using the image data, the surface reflectance parameters including at least one specular reflectance parameter.

28. A computer-readable medium having stored therein computer-readable instructions for a processor, wherein the instructions, when read and implemented by the processor, cause the processor to:
input and store data representative of a plurality of N images of a surface of an object, wherein said data are generated by a camera configured to receive light reflected from the surface while an elongated light source is moved so that light from the light source sweeps across the surface of the object, wherein each image is captured at one of a succession of time points $t_i$ (i=1, . . . , N) within he time period, and wherein each image comprises a plurality of pixels, each pixel having an associated pixel value that represents the image brightness of a corresponding surface unit area on the surface of the object;
measure a reflectance trace for each pixel, wherein the measured reflectance trace of a pixel is a function of the detected intensity, at each time point $t_i$ (i=1, . . . N), of light reflected from the surface unit area corresponding to the pixel;
compute a table of synthesized reflectance traces wherein each synthesized reflectance trace in the table is representative of the intensity, at each time point, of light originating from a virtualized rendition of said light source and reflected from the surface unit area corresponding to the pixel, and wherein each synthesized reflectance trace is computed using one of a predetermined set of model surface reflectance parameters; and
compare for each pixel the measured reflectance trace to the table of synthesized reflectance traces so as to determine the surface reflectance parameters that best fit the measured reflectance trace.

29. A method of determining one or more surface reflectance parameters of an object, comprising:
moving an extended light source along a trajectory during a time period so that light from said light source sweeps across the surface of an object during the time period, said light source having an elongated configuration and extending from one end to another;
receiving, during the time period, light reflected from the surface and generating a plurality of N images from the received light, each image being generated at one of a succession of time points $t_i$ (i=1, . . . N) within the time priod, each image comprising a plurality of pixels wherein each pixel has an associated pixel value that represents the image brightness of a corresponding surface unit area or the surface of the object;
measuring a reflectance trace for each pixel, wherein the reflectance trace is representative of the recorded intensities at each time pont $t_i$ (i=1, . . . N) of light reflected from the surface unit area corresponding to said pixel;
computing a table of synthesized reflectance trace, wherein each reflectance trace in said table is computed using one of a predetermined set of model surface reflectance parameters; and
comparing for each pixel said measured reflectance trace to said table of synthesized reflectance traces so as to determine the surface reflectance parameters that best fit said measured reflectance trace.

30. A method in accordance with claim 29, wherein said surface reflectance parameters comprise at least:
a diffuse reflectance parameter $\rho_d$ representative of the proportion of light incident on said surface that is scattered substantially omni-directionally while being reflected;
a specular reflectance parameter $\rho_s$ representative of the proportion of light incident on the surface that is reflected substantially in a mirror direction with respect to the angle of incidence; and
a specular roughness parameter a representative of the roughness of said surface.

31. A method in accordance with claim 29, further comprising:
projecting a plane of laser light onto at least a porton of said surface while said light source is moved along said trajectory and said plurality of images are generated during said time period; and
observing a laser stripe that appears in each of said plurality of images as a result of said projection of said plane of laser light to determine the surface height for each point on said surface.

32. A method in accordance with claim 29, further comprising: illuminating at least a portion of the surface of the object from behind the object with respect to an optical imaging system configured to detect light transmitted through the object while illuminated from behind; and
computing a translucency parameter $\rho_{trans}$ for one or more areas of interest on the surface of the object based on the intensity of the transmitted light at each pixel.

33. A reflectometry apparatus in accordance with claim 1, wherein said actuator is configured to move the light source along two or more trajectories during two or more corresponding time period so that light from said light source sweeps across the surface of the object during each time period; and
wherein said optical imaging system is configured to receive light reflected from the surface of the object during each time period, and to generate therefrom image data representative of a plurality of images of the surface of the object.

* * * * *

UNITED STATES PATENT AND TRADEMARK OFFICE
CERTIFICATE OF CORRECTION

PATENT NO. : 6,919,962 B2
DATED : July 19, 2005
INVENTOR(S) : Debevec, Paul E., et al.

It is certified that error appears in the above-identified patent and that said Letters Patent is hereby corrected as shown below:

Column 1,
Line 4, add the following:
-- GOVERNMENT'S INTEREST IN APPLICATION

This invention was made with government support under Contract No. DAAD 19-99-D-0046-0004 awarded by the United States Army. The government has certain rights in the invention. --.

Signed and Sealed this

Twenty-eighth Day of February, 2006

JON W. DUDAS
*Director of the United States Patent and Trademark Office*